United States Patent [19]
Geiler et al.

[11] Patent Number: 5,408,327
[45] Date of Patent: Apr. 18, 1995

[54] PROCESS AND ARRANGEMENT FOR PHOTOTHERMAL SPECTROSCOPY

[75] Inventors: Hans-Dieter Geiler; Matthias Wagner, both of Jena, Germany

[73] Assignee: Jenoptik GmbH, Jena, Germany

[21] Appl. No.: 204,386

[22] PCT Filed: Jul. 14, 1993

[86] PCT No.: PCT/EP93/01852
§ 371 Date: Mar. 15, 1994
§ 102(e) Date: Mar. 15, 1994

[87] PCT Pub. No.: WO94/02834
PCT Pub. Date: Feb. 3, 1994

[30] Foreign Application Priority Data
Jul. 16, 1992 [DE] Germany .................. 42 23 337.2

[51] Int. Cl.⁶ .................................. G01N 21/00
[52] U.S. Cl. ........................................ 356/432
[58] Field of Search ............ 250/339.06, 341.6, 341.3; 356/432, 432 T

[56] References Cited
FOREIGN PATENT DOCUMENTS

| | | |
|---|---|---|
| 0233120 | 8/1987 | European Pat. Off. . |
| 0463938 | 1/1992 | European Pat. Off. . |
| 0484282 | 5/1992 | European Pat. Off. . |
| 4109182 | 10/1991 | Germany . |

OTHER PUBLICATIONS

Measurement Science Technology, 1 Dec. 1991, pp. 1088–1093, Wagner, et al "Single Beam Thermowave Analysis, Etc.".
Review of Scientific Instruments, 1 Jan. 1990, pp. 101–113, Power, "Amplitude and Phase Modulation (AM-PM) Wide Band Photothermal Spectrometry: III Experiment".

Primary Examiner—Richard A. Rosenberger
Assistant Examiner—Robert Kim
Attorney, Agent, or Firm—McAulay Fisher Nissen Golberg & Kiel

[57] ABSTRACT

A process and arrangements for photothermal spectroscopy (thermal wave analysis) by the single-beam method with double modulation technique. A single-beam method is developed making use of the advantages of double modulation technique in detecting the photothermally generated difference frequency without requiring partial beams and while achieving extensive absence of intermodulation, the intensity of the laser beam is modulated before striking the object in such a way that the modulation spectrum substantially contains a carrier frequency ($f_1$) and two sideband frequencies ($f_1 \pm F_2$), wherein $f_2$ is the base clock frequency of the modulation, a regulating detector and a control loop intervening in the modulation process suppress that component of the base clock frequency ($f_2$) in the same phase with the mixed frequency of the carrier frequency and sideband frequencies. After interaction with the object the optical response of the object is measured by means of a measurement detector and frequency-selective and phase-selective device as the amplitude of that component of the base clock frequency ($f_2$) which, as the photothermal mixed product, has the same phase as the mixed frequency of the carrier frequency ($f_1$) and sideband frequency ($f_1 \pm f_2$). Use for nondestructive and noncontact analysis of the material parameters of areas of solid bodies close to the surface is described.

30 Claims, 5 Drawing Sheets

PROCESS AND ARRANGEMENT FOR PHOTOTHERMAL SPECTROSCOPY

BACKGROUND OF THE INVENTION a) Field of the Invention

The invention is directed to a process and arrangements for photothermal spectroscopy (thermal wave analysis) based on the single-beam method with double modulation technique. It is applied for measuring geometrical, thermal, electronic and elastomechanical material parameters of surface coats or layers by evaluating the photothermal response signals from areas of solid bodies close to the surface. The noncontact and nondestructive process according to the invention is applied chiefly as a test method for quality control in coating technology.

b) Background Art

Methods of photothermal spectroscopy for noncontact, nondestructive detection of parameters of thin layers are known. The physical principles and fundamentals are compiled and described e.g. in "Photoacoustic and Thermal Wave Phenomena in Semiconductors" A MANDELIS (Ed.), North Holland, N.Y. 1987. In a known method according to ROSENCWAIG, a periodically intensity-modulated pump laser produces a photothermal response in the layer which in turn locally modulates the refractive index so that the modulated optical reflection (MOR) can be measured with a so-called probe laser beam (U.S. Pat. No. 4,579,463). This method accordingly requires two lasers with different wavelengths and a precise alignment of the two beams relative to one another on the sample. In addition to the optical precision of the beam adjustment mentioned above, the solutions suggested in U.S. Pat. No. 4,634,290, U.S. Pat. No. 4,636,088, and EP 0 291 276 involve considerable expense for optical elements for adapting the thickness of the two beam bundles. Further, the inherent noise of the probe laser represents a limiting factor for the resolution capability requiring the use of lasers with extensive noise stabilization.

Single-beam methods are also known for measuring the MOR (CHEN et al., Appl. Phys. Lett. 50 (1984) 1349; A. LÖRINCZ, L. ANDOR, Appl. Phys. B 47 (1988) 35; M. WAGNER, H. D. GEILER, Meas. Sci. Technol. 2 (1991) 1088). To separate the MOR from the reflected modulated pump intensity, LÖRINCZ makes use of the fact that the photothermal response causes harmonic waves (second harmonic) in the reflected component which can be detected by lock-in detection. However, the requisite absence of harmonic waves of $10^{-7}$ cannot be achieved because of the finite nonlinearities of the modulator. This is also true with respect to compensating for noise. In the method used by WAGNER, this disadvantage is overcome by applying double modulation technique in which two modulation frequencies are impressed on the pump beam and sum or difference frequencies produced by the photothermal refractive index modulation in the sample are detected. However, it is only possible to generate the double-modulated beam without intermodulation by combining two separately modulated partial beams. Beyond the extra expenditure on optics for aligning the partial beams, this requires the use of two separate optical modulation systems. In particular, the return of the modulated partial beam components into the laser and accordingly internal modulation of the latter must be prevented. This requires expensive optical insulators.

OBJECT AND SUMMARY OF THE INVENTION

The object of the present invention is to develop a single-beam method which makes use of the advantages of double modulation technique without requiring partial beams and which achieves a high degree of freedom from intermodulation.

The basic idea of the invention consists in that the stimulation of the object and the detection of the transmission or reflection modulated by the object is effected with an individual optical beam directed on the object, the intensity of the beam being substantially modulated with three frequencies, one of which is the arithmetical mean of the other two frequencies. Thus, the modulation spectrum substantially includes a carrier frequency and its first two sideband frequencies at a distance from a base frequency. The thermal wave reaction induced in the object by means of an optical beam modulated with this frequency spectrum takes place in the radiation leaving the object (directed, transmitted or reflected component, scatter radiation, heat radiation) in the form of mixed products of the three frequencies from which the base frequency is detected by means of a frequency-selective and phase-selective measuring device and serves as a measurement of the linear response of the object.

The base frequency is advisedly as small as possible so that the object is effectively stimulated with the carrier frequency $f_1$, i.e. the photothermal dispersion in the vicinity of the carrier frequency is negligible and the frequency to be detected is in the lower frequency range which can be managed easily in terms of technique.

A familiar general problem in intensity modulation of optical radiation is the nonlinear characteristic of the modulator. When using an individual modulating optical element for generating the modulation spectrum according to the invention, these nonlinearities result in the inclusion of frequency mixed products in the beam directed on the object which complicates and distorts the detection of the thermal wave response. For the purposes of the modulation spectrum according to the invention, a frequency corresponding to the base frequency occurs as such a mixed product caused by the nonlinearities of the modulation characteristic line.

The essence of the invention consists in detecting this disturbing signal of the base frequency of the beam directed on the object by means of a regulating detector and removing it via a control loop by manipulating the modulation spectrum by means of a suitable, purposeful change in the electrical signal effecting the modulation. This means that a component of the base frequency is additionally supplied to the modulation process so as to compensate for the unwanted component of this frequency generated by the nonlinearities. This compensation of the modulator nonlinearities is governed by the modulation principle for generating a modulation spectrum.

The object is to produce a time function for the modulation of the laser beam which permits a highly accurate manipulation of the frequency spectrum with a comparatively small expenditure on technical means and, at the same time, offers a high mixing efficiency for detecting the object response.

A modulation signal whose base period T is formed from a base frequency has proven particularly advantageous in this respect. This base period is composed of a (proportional or compact) first period within which there occurs a square-wave modulation of the intensity of the laser beam with a shift of 100% with the carrier frequency, wherein a quantity of periods of duration of the reciprocal carrier frequency corresponding to a whole number is contained in the first partial period, and by a second partial period (occupying the remaining portion of the base time period) in which the intensity of the laser beam is constant.

For an intensity time curve of this type, the frequency component which is in phase with the base frequency is determined in the frequency spectrum substantially by the value of the intensity in the second time segment which is to be adjusted in such a way that the component is zero. For large frequency ratios of the carrier frequency to the base frequency the intensity value to be adjusted corresponds approximately to the arithmetical mean of the intensity formed over the first partial period. Under this condition, the modulation spectrum substantially contains the frequency with two sideband frequencies at a distance from the base frequency of the carrier frequency.

The nonlinear response of the object causes in the radiation leaving the object a change of the original ratio of the mean values of the intensities in the two partial periods of the base period. This change is particularly pronounced when the partial periods are of equal duration. It causes a frequency component to be formed which is in phase with the base frequency. In the frequency diagram, this component is brought about on the nonlinear response characteristic line of the object by mixing the carrier frequency with its first sideband frequencies.

When used for detecting the thermal wave signals, which are usually very small in practice, and accordingly for detecting components of the base frequency it is impossible to effect a static adjustment of the required constant value of the intensity in the second partial period of the base period with the required accuracy. In practice, this means that a frequency component in phase with the base frequency will always inevitably occur. The frequency component in the modulation spectrum of the beam directed on the object, which component is in phase with the base frequency and thus constitutes interference, is positively eliminated, according to claim 1, by means of a control loop which adjusts the required intensity ratios in the two partial periods of the base period, e.g., by means of a corresponding change, in the constant value of the intensity within the second partial period or by changing the first pulse-duty factor within the partial period.

For this purpose, in the regulating process, a portion of the modulated beam is optically decoupled and the component of the unwanted frequency component in phase with the base frequency $f_2$ is determined by means of a photoreceiver (regulating detector) and an additional frequency-selective and phase-selective device. This measurement value is now supplied to the modulator group as an interference variable and causes an exact modulation signal to be generated.

The regulating process described herein has another advantageous result. It not only reduces the unwanted frequency component of the base frequency produced during the intensity modulation by nonlinearities in the modulation process, but at the same time also reduces those components of frequency in phase with the base frequency which originate from the noise of the laser beam intensity and raise the sensitivity limit of the process, since they are superimposed on the measurement signal.

Accordingly, compared to known methods for thermal wave analysis, the realization of the process according to the invention on the one hand allows a considerable reduction in cost on optics (only an individual laser source and guidance of an individual optical beam) and on the other hand enables an increase in sensitivity or the possibility of using comparatively noisy laser sources.

The range of uses of the process according to the invention can also be extended to photothermal wave reactions of the object which essentially do not cause any modulation of the transmission or reflection capability or occurring secondary radiation (scattered light, heat radiation), but rather lead to modulation of the position and/or shape of the beam. This is done by inserting diaphragms at a suitable location in the path of the beam influenced by the object for the purpose of trimming the beam depending on position and shape.

The application of the process according to the invention in different arrangements which fully deliver the promised effects may be distinguished substantially according to the techniques by which the intensity modulation and manipulation of the modulation spectrum are realized.

Thus, the modulation signal of the type according to the invention is generated either in that the light from a source is modulated or in that the intensity modulation is produced by suitable modulation of the light of two beams and the beam directed on the object is generated by combining the two partial beams.

The modulation spectrum is influenced either in that a correction signal is additionally supplied to the element used for intensity modulation or in that an additional optical element supplied with a correction signal is inserted in the beam path.

For a better understanding of the present invention, reference is made to the following description and accompanying drawings while the scope of the invention will be pointed out in the appended claims.

DESCRIPTION OF THE PREFERRED EMBODIMENTS

Figure 1:
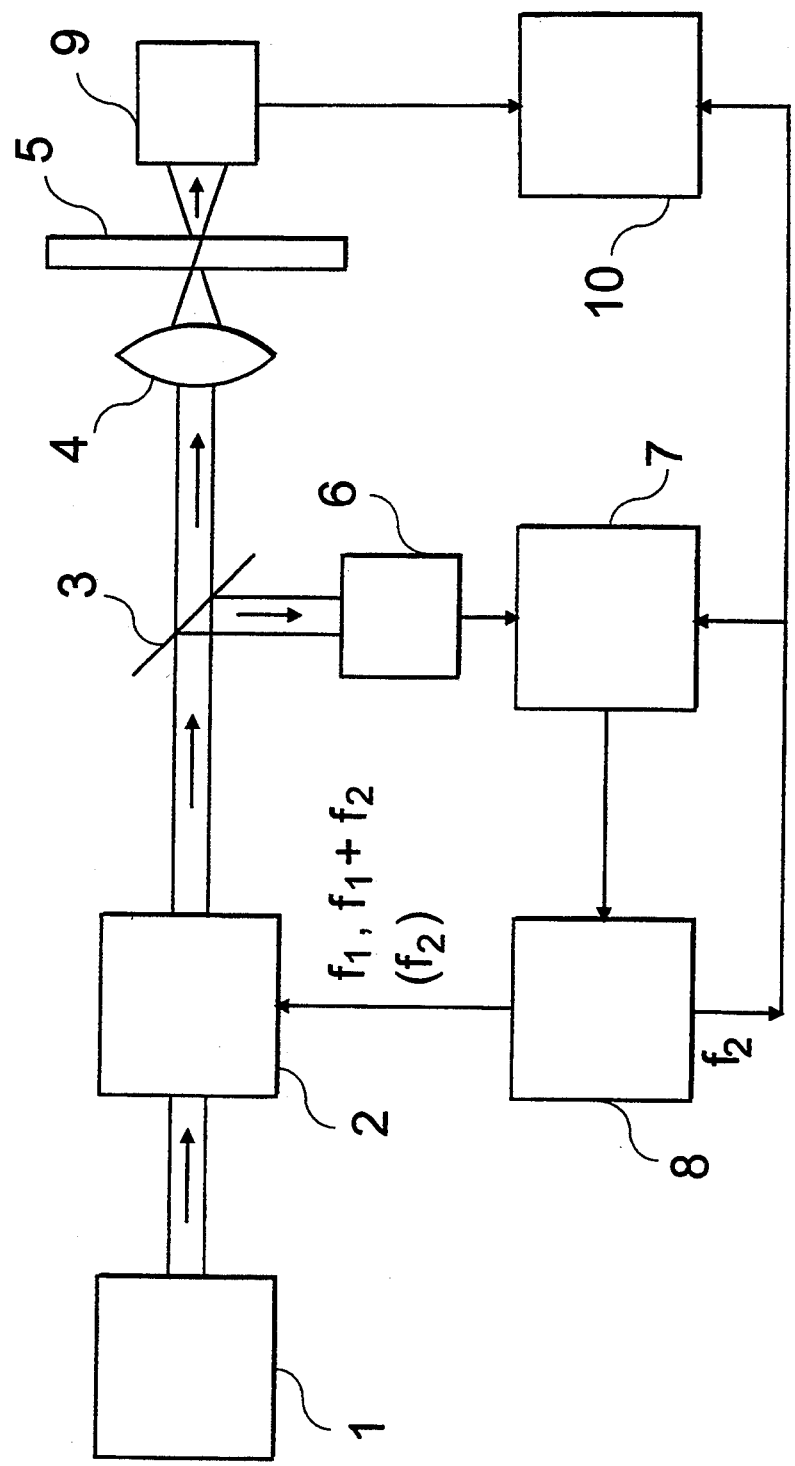
FIG. 1 shows the basic construction, according to the invention, of an arrangement for thermal wave analysis in the transmission variants using a laser source 1 for generating beams and an acousto-optical modulator 2 for intensity modulation.

In the arrangement according to FIG. 1, the laser beam is generated by an optional laser source 1 and passes through an acousto-optical modulator 2 for intensity modulation, the latter being supplied substantially with the modulation frequencies $f_1$ and $f_1 \pm f_2$ from an electronic modulator group 8. The modulated beam, which is focussed with the focusing lens 4, impinges on the object 5 whose response is to be determined.

Before the laser beam strikes the object 5, a component of this laser beam is decoupled to a photoreceiver serving as regulating detector 6 by means of a beam splitter 3. The component of the unwanted component of the base frequency $f_2$ is measured in the modulated optical beam by means of a lock-in amplifier 7, which acts as a frequency selective and phase selective device and whose frequency and phase are tuned to the base frequency $f_2$ likewise supplied by the modulator group 8. The measurement value is fed to the group 8 as an interference variable and causes to be generated therein a modulation component with base frequency $f_2$ which is likewise supplied to the acousto-optical modulator 2.

The acousto-optical modulator 2, regulating detector 6, lock-in amplifier 7, and electronic modulator group 8 form a control loop which causes a component of frequency $f_2$ to be supplied to the acousto-optical modulator which component is defined in such a way that the component of the base frequency $f_2$ produced from the carrier and sideband frequencies $f_1$ and $f_1 \pm f_2$ by its modulation nonlinearities is precisely compensated for. In this way, the modulation spectrum of the beam directed on the object 5 does not contain the base frequency $f_2$.

The component of base frequency $f_2$ produced in the object 5 as a result of the photothermal modulation of the refractive index by mixing the carrier frequency $f_1$ with its first sideband frequencies $f_1 \pm f_2$ is determined by a photoreceiver serving as measurement detector and by a lock-in detector 10 which is likewise tuned in frequency and phase to the base frequency $f_2$ supplied by the modulator group 8.

Figure 2:
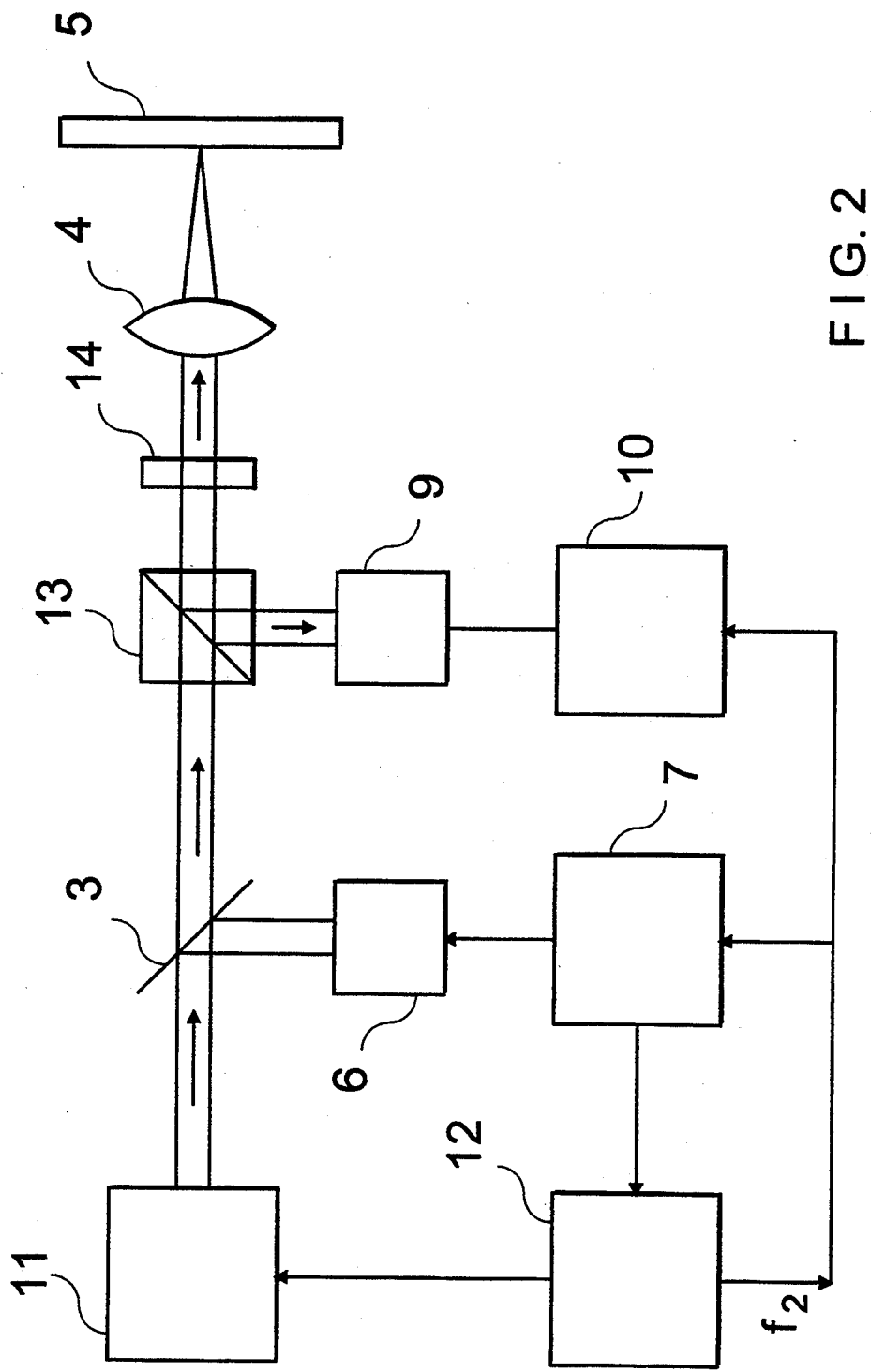
FIG. 2 shows the basic construction, according to the invention, of an arrangement for thermal wave analysis in the reflection variants using a laser diode 11 and the special square-wave modulation of the intensity for generating the modulated laser beam.

In the arrangement according to FIG. 2, a linearly polarized laser beam is generated by a laser diode 11 and directed on the object 5 through the focusing lens 4. Before the laser beam strikes the object 5, a portion of this beam is decoupled by means of a beam splitter 3 to a photoreceiver serving as a regulating detector 6 as set forth in the first example.

Figure 3:
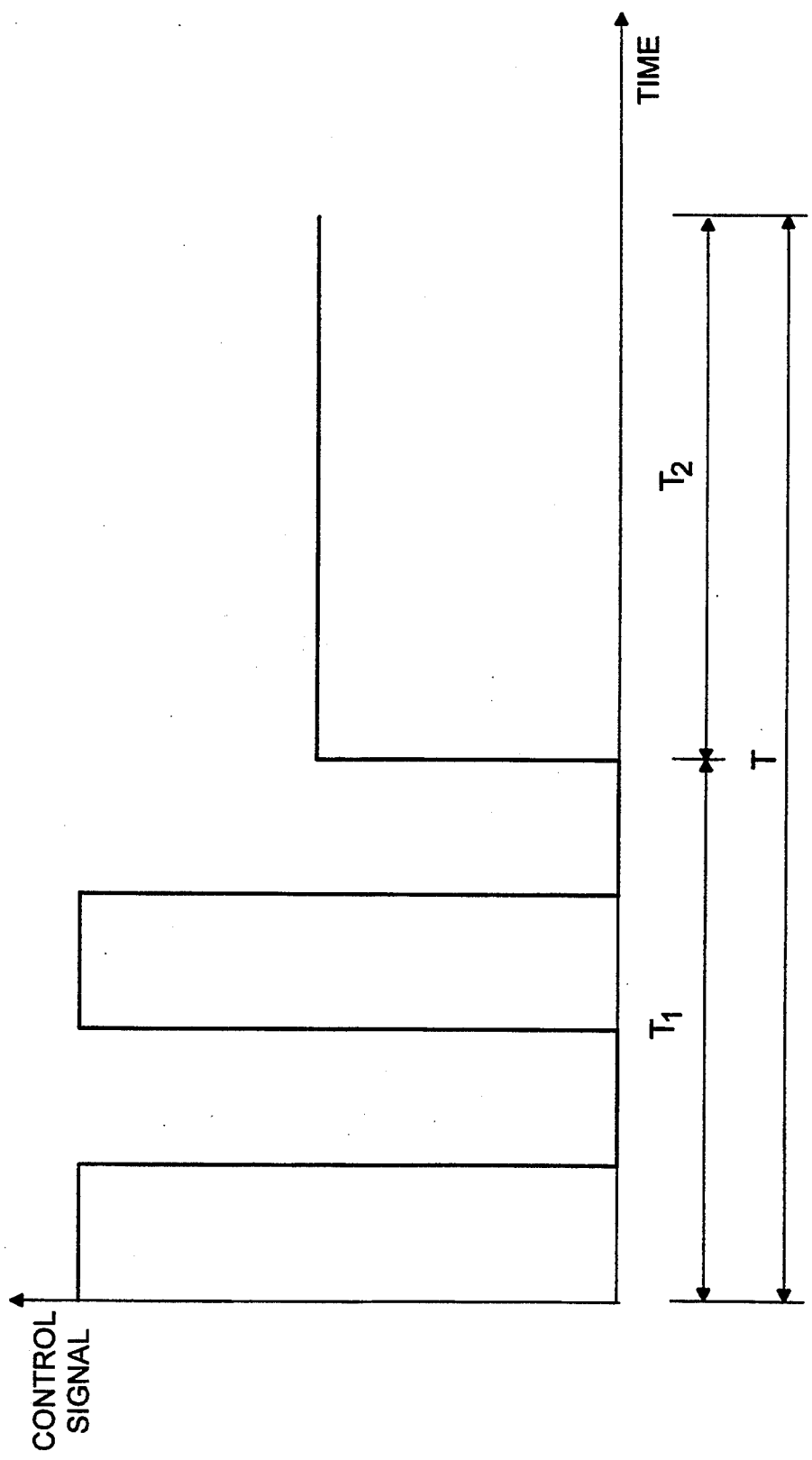
FIG. 3 shows the control signal supplied to the laser diode 11 in FIG. 2 as a function of time.

For the purpose of intensity modulation, the signal shown in FIG. 3 is supplied to the laser diode by an electronic modulator group 8. The time segments $T_1$ and $T_2$ are of identical length for this signal. The electronic modulator group 12 has a control input for adjusting the strength of the signal generated in the time segment $T_2$.

In order to suppress the unwanted interference frequency in phase with the base frequency $f_2$ in the beam directed on the object 5, the regulating detector 6 and the lock-in amplifier 7 which is tuned to the base clock frequency $F_2 = 1/T_2$ with respect to frequency and phase position (see FIG. 3) generate an interference signal which changes the strength of the signal generated in time segment $T_2$ via the control input of the modulator group 8, so that the component of base frequency $f_2$ in the modulated beam is changed. This control loop removes the unwanted component of base frequency $f_2$ from the modulation spectrum. Before impinging on the object 5, the modulated beam which is generated in this way passes through a polarizing splitter 13 and a $\lambda/4$-wave plate 14. The beam component reflected by the object 5 is guided to the photoreceiver 9 serving as measurement detector 9 by means of the polarizing splitter 13.

The nonlinear optical response of the object 5 is then determined, as set forth in the first example, by means of the lock-in detector 10 which is tuned in frequency and phase to the base frequency $f_2$ supplied by the modulator group 8.

Figure 4:
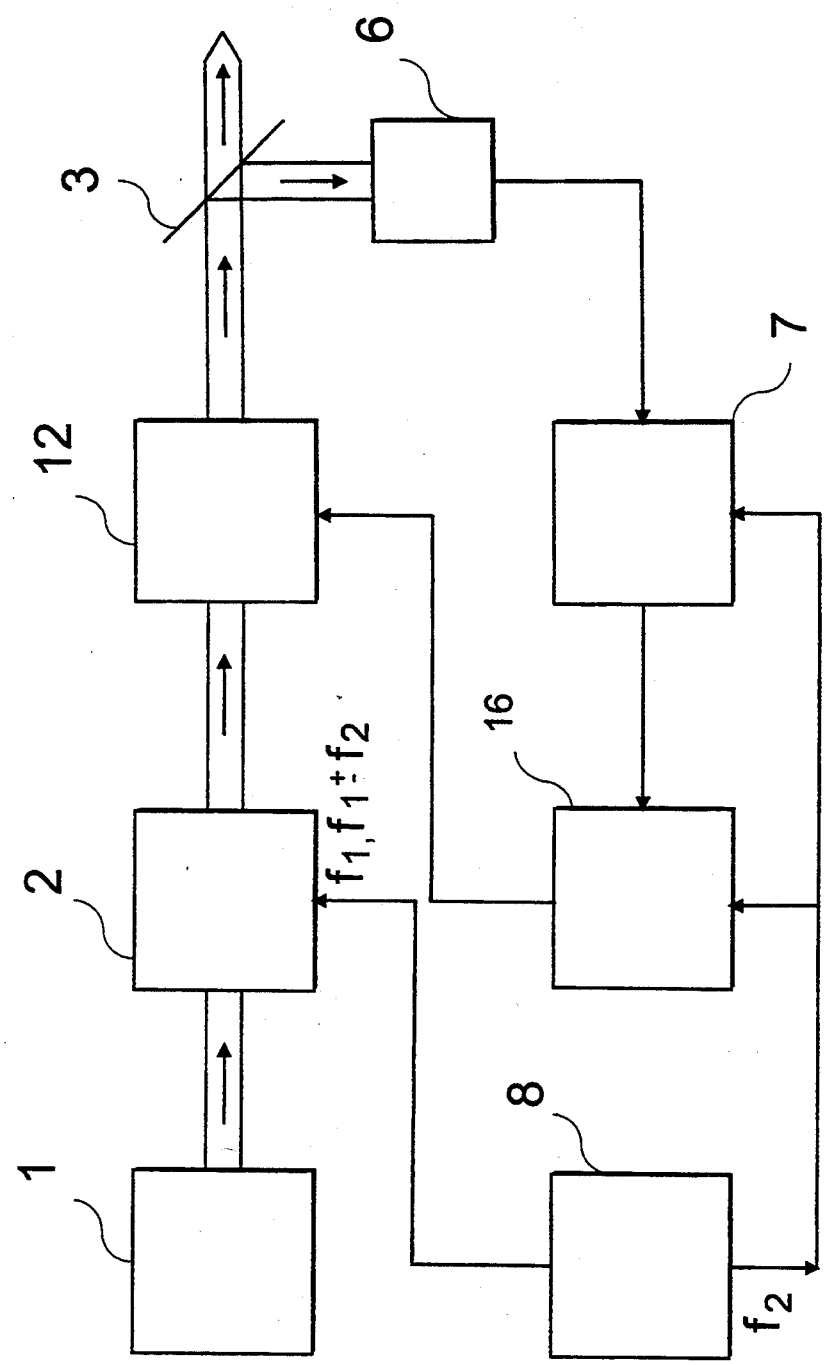
FIG. 4 shows a special embodiment form of the portion for generating the modulated laser beam by means of two acousto-optical modulators 2 and 12, which are arranged one after the other in the beam path.

FIG. 4 shows an arrangement for generating the modulated beam in which the unwanted component of frequency $f_2$ in the modulated beam is corrected by using two acousto-optical modulators. The laser beam is generated by the laser source 1 and first passes through the acousto-optical modulator 2 which is supplied with frequencies $f_1$ and $f_1 \pm f_2$ by the modulator group 8 as was described with reference to the first embodiment example. This modulator group also provides the base frequency $f_2$.

The beam then passes through another acousto-optical modulator 12. This modulator is supplied, via another electronic modulator group 16, with a modulation signal of base frequency $f_2$ which is derived from the signal of base frequency $f_2$ supplied by the modulator group 8 and whose amplitude can be changed via a control input.

A portion of the modulated laser beam is decoupled via the beam splitter 3 to the regulating detector 6. As was already described in the preceding examples, an interference signal is formed by means of the lock-in amplifier 7 which is tuned in frequency and phase to the base frequency $f_2$ supplied by the modulator group 8. Via the control input of the modulator group 16, this interference signal controls the amplitude of the additional modulation of the laser beam with the base frequency $f_2$ effected by the acousto-optical modulator 12. In so doing, the control is effected so as to compensate for the unwanted component of the base frequency $f_2$ in the beam.

Figure 5:
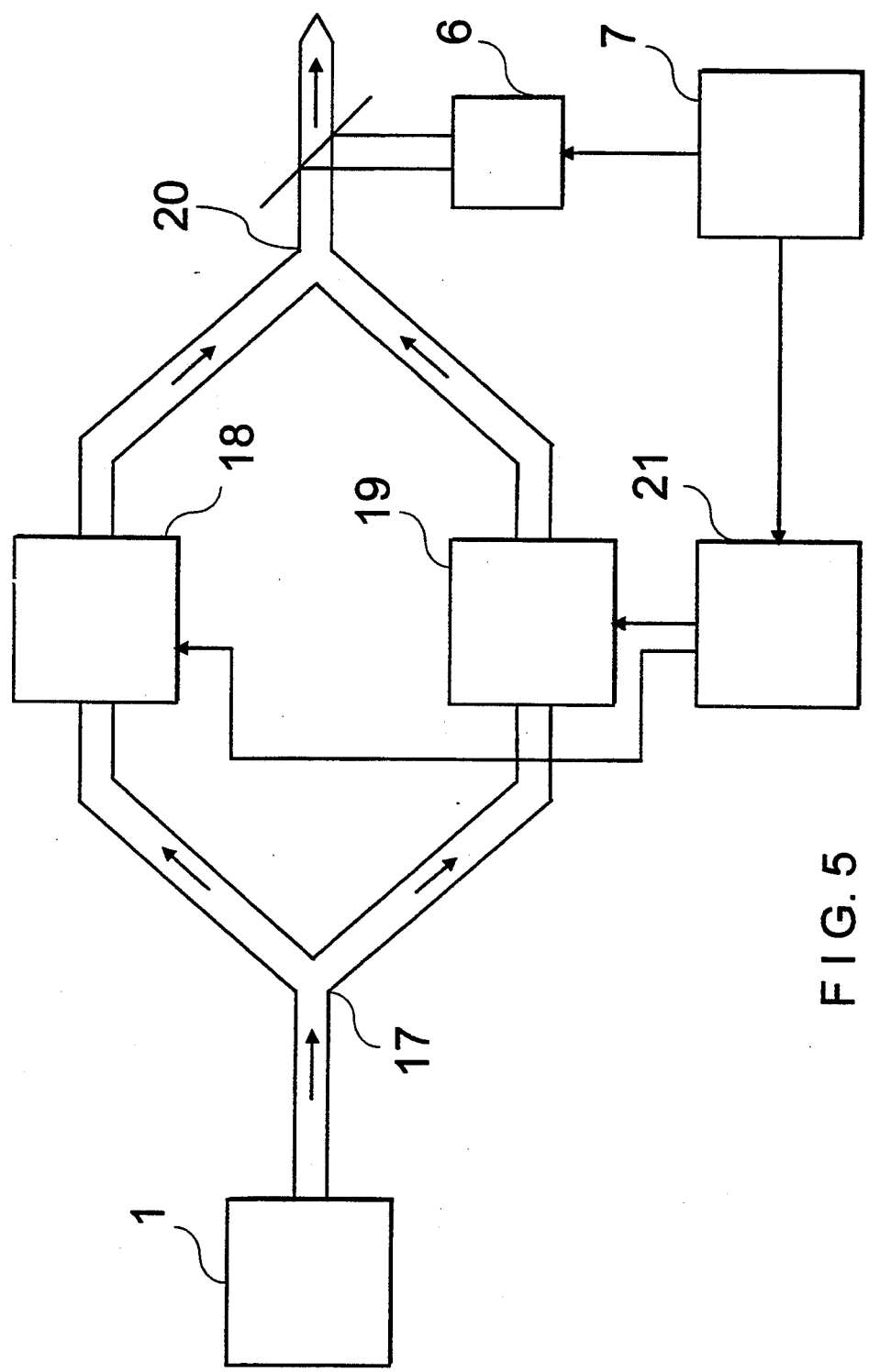
FIG. 5 shows a special embodiment form of the portion for generating the modulated laser beam, by means of an integrated-optical arrangement using an optical frequency modulator.

FIG. 5 shows an integrated-optical realization of the modulation principle. The laser beam is generated by the laser source 1 and split into two partial beams by means of a 3 dB expander 17. One of the two partial beams passes through a controllable optical phase shifter 18, and the other partial beam passes through an optical frequency modulator 19. The two partial beams are then reunited by another 3dB expander 20. The laser beam is modulated in that the modulation period of duration $T = 1/f_2$ is composed of time segments $T_1$ and $T_2$. The optical frequency modulator 19 is acted upon within $T_1$ by the electronic modulator group 21 with a control signal such that the optical frequency of the partial beam passing through the optical frequency modulator 19 is offset by the value of frequency $f_1$ from the optical frequency of the original laser beam. After the two partial beams are united in the expander 20, a laser beam is formed whose intensity is modulated with carrier frequency $f_1$.

Within $T_2$, the electronic modulator group 21 forms a control signal such that the frequency displacement of the two partial beams is zero. Accordingly, after the two partial beams are joined in the expander 20, a beam is formed with an intensity which is constant with respect to time and whose level depends on the optical phase displacement of the two partial beams. Within time segment $T_2$, the electronic modulator group 21 controls the optical phase shifter 18 in such a way that a determined phase displacement is adjusted which leads to the intensity required for eliminating the interfering component of base frequency $f_2$.

As set forth in the preceding examples, this control is carried out in the form of a control loop by way of detecting the interfering component of base frequency $f_2$ in the modulated beam.

While the foregoing description and drawings represent the preferred embodiments of the present invention, it will be obvious to those skilled in the art that various changes and modifications may be made therein without departing from the true spirit and scope of the present invention.

What is claimed is:

1. A process for photothermal spectroscopy in which an intensity-modulated laser beam is directed on an object to be examined and in which, as a result of a reaction of the object to energy applied by the laser beam after interaction with the object, an additional modulation of the intensity is determined as an optical response of the object by a measurement detector, comprising the steps of performing:

a) intensity modulation of the laser beam before it impinges on the object, whose modulation spectrum substantially contains only a carrier frequency ($f_1$) and two sideband frequencies ($f_1 \pm f_2$), the sideband frequencies ($f_1 \pm f_2$) resulting as an amplitude modulation of a base frequency ($f_2$), b) eliminating a component of the base frequency ($f_2$) having the same phase as a mixed frequency resulting from the carrier frequency ($f_1$) and sideband frequencies ($f_1 \pm f_2$) by means of feeding back said detected component as an interference variable to the modulation step, and c) measuring the amplitude of that component of the base frequency ($f_2$) which is contained in the beam leaving the object as a photothermal modulation product in phase with the mixed frequency of the carrier frequency ($f_1$) and sideband frequencies ($f_1 \pm f_2$) by the use of a frequency-selective and phase-selective device.

2. The process according to claim 1, wherein the phase relation of frequency $f_1$ and its sidebands $f_1 \pm f_2$ is periodically reversed by 180° at a frequency which is less than frequency $f_2$.

3. The process according to claim 1, wherein the component of frequency $f_2$ which is contained in the modulation spectrum of the intensity of the laser beam directed on the object and in quadrature with the mixed frequency of the carrier frequency and sideband frequencies is also detected by means of another frequency-selective and phase-selective device and is supplied as an interference signal to another control loop influencing the modulation spectrum for the purpose of adjusting the detected component to the value of zero.

4. The process according to claim 1, wherein the laser beam is generated by an intensity-modulated laser diode.

5. The process according to claim 1, wherein the laser beam passes one or more optical modulators in the beam path between the laser source and the object.

6. The process according to claim 1, wherein the intensity modulation is effected in that the laser beam is composed of two partial beams susceptible to interference, the mean values of the optical frequencies of the two partial beams differing by the value of frequency $f_1$, and the optical frequency of one partial beam is frequency-modulated with a signal of the base frequency $f_2$.

7. The process according to claim 1, wherein the intensity modulation is effected in that the laser beam is composed of two partial beams susceptible to interference, the mean values of the optical frequencies of the two partial beams differing by the value of frequency $f_1$, and the optical phase position of one partial beam is phase-modulated with a signal of base frequency $f_2$.

8. The process according to claim 1, wherein the intensity modulation of the laser beam is effected in such a way that a modulation period of duration $T = 1/f_2$ comprises a time segment of duration $T_1$, in which the intensity is modulated with a periodic signal of carrier frequency $f_1$, and a time segment of duration $T_2$, in which the intensity is constant, and its value is adjusted by said control loop so that the component of the frequency spectrum in phase with frequency $f_2$ has an intensity of zero.

9. The process according to claim 8, wherein an integral number of periods of duration $1/f_1$ is contained within the time segment $T_1$.

10. The process according to claim 9, wherein the modulation with frequency $f_1$ within time segment $T_1$ is effected in such a way that the start of this time segment does not coincide with a zero axis crossing of the oscillation of frequency $f_1$.

11. The process according to claim 3, wherein the influencing of the modulation spectrum by changing the time period is effected between the start of time segment $T_1$ and the zero axis crossing of the oscillation of frequency $f_1$.

12. The process according to claim 8, wherein the time segments $T_1$ and $T_2$ are of equal duration.

13. The process according to claim 8, wherein the influencing of the modulation spectrum by changing the intensity is effected within time segment $T_2$.

14. The process according to claim 8, wherein a square-wave modulation is effected within the time segment $T_1$.

15. The process according to claim 14, wherein the modulation spectrum is influenced by changing the pulse-duty factor.

16. The process according to claim 14, wherein the modulation spectrum is influenced by changing the rise time and fall time of the square-wave pulses.

17. The process according to claim 6, wherein a modulation form is produced in that the laser beam is composed of two partial beams susceptible to interference, the optical frequency of one partial beam being modulated with a signal of period T in such a way that it differs from the optical frequency of the other partial beam in time segment $T_1$ by the value of frequency $f_1$.

18. The process according to claim 7, wherein a modulation form is produced in that the laser beam is composed of two partial beams susceptible to interference, the optical phase position of one partial beam being modulated with a signal of period T in such a way that the phase difference changes periodically relative to the other partial beam in time segment $T_1$ with the base frequency $f_1$ and remains constant in time portion $T_2$.

19. The process according to claim 1, wherein a proportion of the light directed on the object is decoupled to a reference detector for generating a reference value and the differential signal is evaluated by the measurement detector and reference detector.

20. The process according to claim 19, wherein a regulating detector is also used simultaneously as a reference detector.

21. In an arrangement for photothermal spectroscopy in which an intensity-modulated laser beam is directed on an object to be examined and in which, as a result of a reaction of the object to energy applied by the laser beam after interaction with the object, an additional modulation of the intensity is determined as an optical response of the object by a measurement detector, the improvement comprising:
 a) means for performing intensity modulation of the laser beam before it impinges on the object, whose modulation spectrum substantially contains only a carrier frequency ($f_1$) and two sideband frequencies ($f_1 \pm f_2$), the sideband frequencies ($f_1 \pm f_2$) resulting as an amplitude modulation of a base frequency ($f_2$);
 b) means for eliminating a component of the base frequency ($f_2$) having the same phase as a mixed frequency resulting from the carrier frequency ($f_1$) and sideband frequencies ($f_1 \pm f_2$) by means of feeding back said detected component as an interference variable to the modulation means; and
 c) means for measuring the amplitude of that component of the base frequency ($f_2$) which is contained in the beam leaving the object as a photothermal modulation product by the use of a frequency-selective device.

22. The arrangement of claim 21, wherein said amplitude measuring means measures the photothermal modulation product in phase with the mixed frequency of the carrier frequency ($f_1$) and sideband frequencies ($f_1 \pm f_2$) wherein the device is also phase selective.

23. The arrangement of claim 21, wherein said means for eliminating a component of the base frequency includes a semireflecting mirror arranged after the modulation means for decoupling a partial beam of the modulated laser beam to a regulating detector, said regulating detector being connected with an electronic modulator group at an output side via a lock-in amplifier acting as a frequency-selective and phase-selective device, said modulator group being coupled to a control input of said modulator means.

24. The arrangement of claim 22, wherein said means for measuring includes a lock-in detector acting as a frequency-selective and phase-selective device and being arranged in the beam path after interaction of the laser beam with the object, said lock-in detector is adapted to be timed to the base frequency.

25. The arrangement of claim 21, wherein said laser source and modulator means are combined in an intensity-modulated laser diode.

26. In an arrangement for photothermal spectroscopy in which an intensity-modulated laser beam is directed on an object to be examined and in which, as a result of a reaction of the object to energy applied by the incident laser beam, the object impresses an additional modulation of intensity on the laser beam in the path of the beam after interaction with the object, a measurement detector being arranged for detecting this additional modulation as an optical response of the object, the improvement comprising:
 a laser source and a modulator which are provided for generating the intensity-modulated laser beam, said modulator having a modulation spectrum substantially containing only three frequencies in the form of the carrier frequency ($f_1$) with the first sidebands ($f_1 \pm f_2$), which three frequencies result from a carrier frequency ($f_1$) and a base frequency ($f_2$);
 a semireflecting mirror which is arranged after the modulator for decoupling a partial beam of the modulated laser beam to a regulating detector, said regulating detector being connected with an electronic modulator group at the output side via a lock-in amplifier acting as a frequency-selective and phase-selective device, said modulator group being coupled to the control input of the modulator for supplying an appropriate interference signal of the base frequency ($f_2$) so as to compensate for an unwanted component of the base frequency ($f_2$) produced from the carrier frequency ($f_1$) and sideband frequencies ($f_1 \pm f_2$) by modulation nonlinearities; and
 a measurement detector having an output which is connected with a lock-in detector acting as a frequency-selective and phase-selective device, said measurement detector being arranged in the beam path after interaction of the laser beam with the object, said lock-in detector of the modulator group being adapted or tuned to the base frequency ($f_2$) which is generated as a result of photothermal modulation of the index of refraction by mixing the carrier frequency ($f_1$) and sideband frequencies ($f_1 \pm f_2$) in the object.

27. The arrangement according to claim 26, wherein said laser source and modulator are combined in an intensity-modulated laser diode which is controlled by the modulator.

28. The arrangement according to claim 25, wherein another modulator is arranged directly downstream of said modulator and is controlled by a modulation signal of the base frequency ($f_2$) which is variable with respect to amplitude, wherein another modulator group is provided for controlling, which modulator group is connected on the input side with the base ($f_2$) supplied by the modulator group and which has control input, the lock-in amplifier providing a corresponding regulating variable via said control input for regulating the amplitude.

29. In an arrangement for photothermal spectroscopy in which an intensity-modulated laser beam is directed on an object to be examined and in which, as a result of a reaction of the object to energy applied by the incident laser beam, the object impresses an additional modulation of intensity on the laser beam in the path of the beam after interaction with the object, a measurement detector is arranged for detecting this additional modulation as an optical response of the object, the improvement comprising:
 a laser source and an optical phase shifter and optical frequency modulator, which are provided for generating the intensity modulated beam, said elements providing means for effecting the intensity modulation of the laser beam in such a way that a modulation period of duration $T = 1/f_2$, where $f_2$ is a base frequency, comprises a time segment duration $T_1$, in which the intensity is modulated with a periodic signal of carrier frequency $f_1$, and a time segment duration $T_2$, in which the intensity is constant;
 a semireflecting mirror being arranged in the intensity-modulated laser beam prior to interaction with the object for decoupling a beam to a regulating detector, and the regulating detector being connected with the electronic modulator group at the output side via a lock-in amplifier acting as a frequency-selective and phase-selective device, wherein the modulator group supplies a control signal to the phase shifter such that the phase displacement results in an intensity value for the elimination of an interfering component of the base frequency ($f_2$); and a measurement detector having an output which is coupled to a lock-in detector acting as a frequency-selective and phase-selective device, said detector beam being arranged in the beam path after interaction of the laser beam with the object, wherein the lock-in detector of the modulator group is adapted or tuned to the base frequency ($f_2$) which is generated as a result of photothermal modulation of the index of refraction by mixing the carrier frequency ($f_1$) and sideband frequencies ($f_1 \pm f_2$) in the object.

30. The arrangement according to claim 29, wherein the phase shifter and frequency modulator are realized in integrated optics and a 3-dB expander is arranged for splitting and recombining the beam.

* * * * *